(12) United States Patent
Pesu

(10) Patent No.: US 8,844,837 B1
(45) Date of Patent: Sep. 30, 2014

(54) FRAGRANCE VAPOR DISPENSER

(76) Inventor: Brad Pesu, Gilbert, AZ (US)

(*) Notice: Subject to any disclaimer, the term of this patent is extended or adjusted under 35 U.S.C. 154(b) by 905 days.

(21) Appl. No.: 13/023,212

(22) Filed: Feb. 8, 2011

Related U.S. Application Data

(63) Continuation-in-part of application No. 12/214,442, filed on Jun. 18, 2008, now abandoned.

(60) Provisional application No. 61/427,672, filed on Dec. 28, 2010.

(51) Int. Cl.
*A24F 25/00* (2006.01)

(52) U.S. Cl.
USPC .................. 239/45; 239/44; 239/71; 239/73; 239/289; 422/125

(58) Field of Classification Search
USPC ............... 239/44–51.5, 71, 73, 289; 422/125
See application file for complete search history.

(56) References Cited

U.S. PATENT DOCUMENTS

| | | | | |
|---|---|---|---|---|
| 2,471,949 | A | * | 5/1949 | Gilowitz .......................... 239/44 |
| 3,861,991 | A | * | 1/1975 | Kim ................................ 428/13 |
| 4,913,350 | A | * | 4/1990 | Purzycki ......................... 239/44 |
| 7,819,336 | B2 | * | 10/2010 | Newman .......................... 239/44 |
| 8,235,308 | B2 | * | 8/2012 | Gaines et al. .................... 239/44 |
| 8,540,168 | B2 | * | 9/2013 | Bennett et al. ................... 239/43 |
| 2007/0187524 | A1 | * | 8/2007 | Sherwood ........................ 239/54 |
| 2009/0101729 | A1 | * | 4/2009 | Newman .......................... 239/44 |
| 2010/0147969 | A1 | * | 6/2010 | Bennett et al. ..................... 239/6 |

* cited by examiner

*Primary Examiner* — Christopher Kim
(74) *Attorney, Agent, or Firm* — Booth Udall Fuller, PLC

(57) ABSTRACT

A fragrance vapor dispenser that includes synthetic wicks is disclosed. In an implementation, the fragrance vapor dispenser may comprise at least one synthetic wick. The synthetic wick may comprise an annular, longitudinal outer shell and an absorbent portion at least partially within the outer shell. The absorbent portion may also extend from a first longitudinal end to a second longitudinal end of the outer shell. The outer shell may also be more dense than the absorbent portion and sufficiently dense to vertically support the first longitudinal end above the second longitudinal end without additional support above the second longitudinal end. The synthetic wick may also comprise a color band that comprises a colorant absorbed through the outer shell and at least partially absorbed into the absorbent portion. In an implementation, the color band may comprise a width of at least ⅛ inch.

22 Claims, 5 Drawing Sheets

FRAGRANCE VAPOR DISPENSER

CROSS REFERENCE TO RELATED APPLICATIONS

This document claims the benefit of the filing date of U.S. Provisional Patent Application 61/427,672, entitled "ILLUMINATED BASE FOR HOLDING FRAGRANCE DIFFUSERS" to Pesu, which was filed on Dec. 28, 2010, the contents of which are hereby incorporated by reference.

This application is also a continuation-in-part application of the earlier U.S. Utility patent application to Pesu, entitled "FRAGRANCE DIFFUSER USING MULTIPLE THIN ARTIFICIAL WICKS," application Ser. No. 12/214,442, filed Jun. 18, 2008, now pending, the disclosure of which is hereby incorporated herein by reference.

BACKGROUND

1. Technical Field

Aspects of this document relate generally to the field of fragrance diffusers.

2. Background Art

Traditional fragrance diffusers typically consist of a bottle filled with a fragrant solution. Wooden reeds may then be placed in the solution in the bottle to absorb and disperse a fragrant throughout the room. Some diffusers also include a fan to facilitate diffusion of the fragrance into the room.

SUMMARY

Aspects of this disclosure relate to a fragrance vapor dispenser involving at least one wick with at least one color band that causes the wick to change color adjacent to the color band. Other aspects of this disclosure relate to a display table for a fragrance vapor dispenser.

In one aspect, a fragrance vapor dispenser may comprise at least one synthetic wick comprising a length to width ratio of at least 30 and being formed of synthetic fibers, the at least one synthetic wick further comprising a longitudinal outer shell and an absorbent portion at least partially within the outer shell and extending from a first longitudinal end to a second longitudinal end of the outer shell, and at least one color band, wherein the outer shell is more dense than the absorbent portion and sufficiently rigid to vertically support the first longitudinal end above the second longitudinal end without additional support above the second longitudinal end, wherein the at least one color band comprises a colorant absorbed through the outer shell at least partially into the absorbent portion, the color band having a longitudinal width of at least ⅛ inch.

Particular implementations may comprise one or more of the following features. At least a portion of the synthetic wick may be within a fragrance container containing a fragrance solution, the fragrance solution comprising a solvent and a fragrance oil. The solvent may comprise a water-based solvent. The solvent may comprise an organic solvent. A base comprising a substantially planar surface upon which the fragrance container sits and a motor that rotates the substantially planar surface. The base further may comprise at least one light emitting diode (LED) visible through the substantially planar surface, wherein a temperature of the fragrance solution increases when the at least one LED is on. The outer shell and the absorbent portion may be the same synthetic material. The synthetic wick may comprise extruded polypropylene. The synthetic wick further may comprise a porous material. The diameter of the at least one synthetic wick may be between 1/16 inch and ¼ inch. The fragrance solution further may comprise a fragrance solution colorant, wherein the synthetic wick changes color as the fragrance solution is absorbed by the at least one synthetic wick and the fragrance solution dye spreads throughout the wick. At least one second color band on the at least one synthetic wick. The at least one second color band may be spaced more than 1/16" from the first color band. The at least one synthetic wick may be shaped by a molding process.

According to another aspect, a method of dispensing a fragrance vapor may comprise applying a colorant to at least a portion of a longitudinal outer shell of at least one synthetic wick, the at least one synthetic wick comprising a length to width ratio of at least 30 and being formed of synthetic fibers and comprising an absorbent portion at least partially within the outer shell and extending from a first longitudinal end to a second longitudinal end of the outer shell, wherein the outer shell is more dense than the absorbent portion and sufficiently rigid to vertically support the first longitudinal end above the second longitudinal end without additional support above the second longitudinal end, placing a fragrance solution in a fragrance container, the fragrance solution comprising a solvent and a fragrance oil, placing at least one synthetic wick in the fragrance solution, and changing a color of at least a portion of the synthetic wick at a portion of the synthetic wick to which the colorant was not applied as the wick absorbs the fragrance solution adjacent to the portion of the synthetic wick to which the colorant was applied.

Particular implementations may comprise one or more of the following features. Placing the fragrance container on a substantially planar surface of a base, the base comprising at least one light emitting diode (LED) visible through the substantially planar surface and a motor configured to rotate the planar surface. Applying heat to the fragrance solution by turning on the at least one LED increase a rate of fragrance dispersal. Extruding polypropylene to create the synthetic wick.

According to another aspect, a fragrance vapor dispenser may comprise at least one molded wick comprising synthetic fibers, an outer shell, an absorbent portion at least partially within the outer shell and extending from a first end to a second end of the at least one wick, and a color band, wherein the outer shell is more dense than the absorbent portion and sufficiently rigid to vertically support the first end above the second end without additional support for the wick above the second end, and wherein the color band comprises colorant absorbed through the outer shell at least partially into the absorbent portion, the color band having a width of at least ⅛ inch.

Particular implementations may comprise one or more of the following features. At least a portion of the molded wick may be within a fragrance container containing a fragrance solution, the fragrance solution comprising a solvent and a fragrance oil. A base may comprise a substantially planar surface upon which the fragrance container sits, a motor that rotates the substantially planar surface, and at least one light emitting diode (LED) visible through the substantially planar surface.

According to another aspect, a fragrance vapor dispenser may comprise at least one wooden reed, wherein at least a portion of the wooden reed is within a fragrance container containing a fragrance solution, the fragrance solution comprising a solvent and a fragrance oil, and a base comprising a substantially planar surface upon which the fragrance container sits, a motor that rotates the substantially planar surface, and at least one light emitting diode (LED) visible through the substantially planar surface, wherein a temperature of the fragrance solution increases when the at least one LED is on.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

The invention will hereinafter be described in conjunction with the appended drawings, where like designations denote like elements, and.

DESCRIPTION

This application is related to pending U.S. patent application Ser. No. 12/214,442 to Pesu, filed Jun. 18, 2008, the disclosure of which is hereby incorporated herein by reference and provisional U.S. Patent Application No. 61/427,627, filed Dec. 28, 2010, the disclosure of which is also incorporated herein by reference. This disclosure, its aspects and implementations, are not limited to the specific components or assembly procedures disclosed herein. Many additional components and assembly procedures known in the art consistent with the intended synthetic wicks and/or assembly procedures for a fragrance wick and base will become apparent for use with implementations of synthetic wicks and/or bases from this disclosure. Accordingly, for example, although particular synthetic wicks are disclosed, such wicks and implementing components may comprise any shape, size, style, type, model, version, measurement, concentration, material, quantity, and/or the like as is known in the art for such wicks and implementing components, consistent with the intended operation of diffusing fragrances.

Figure 1:
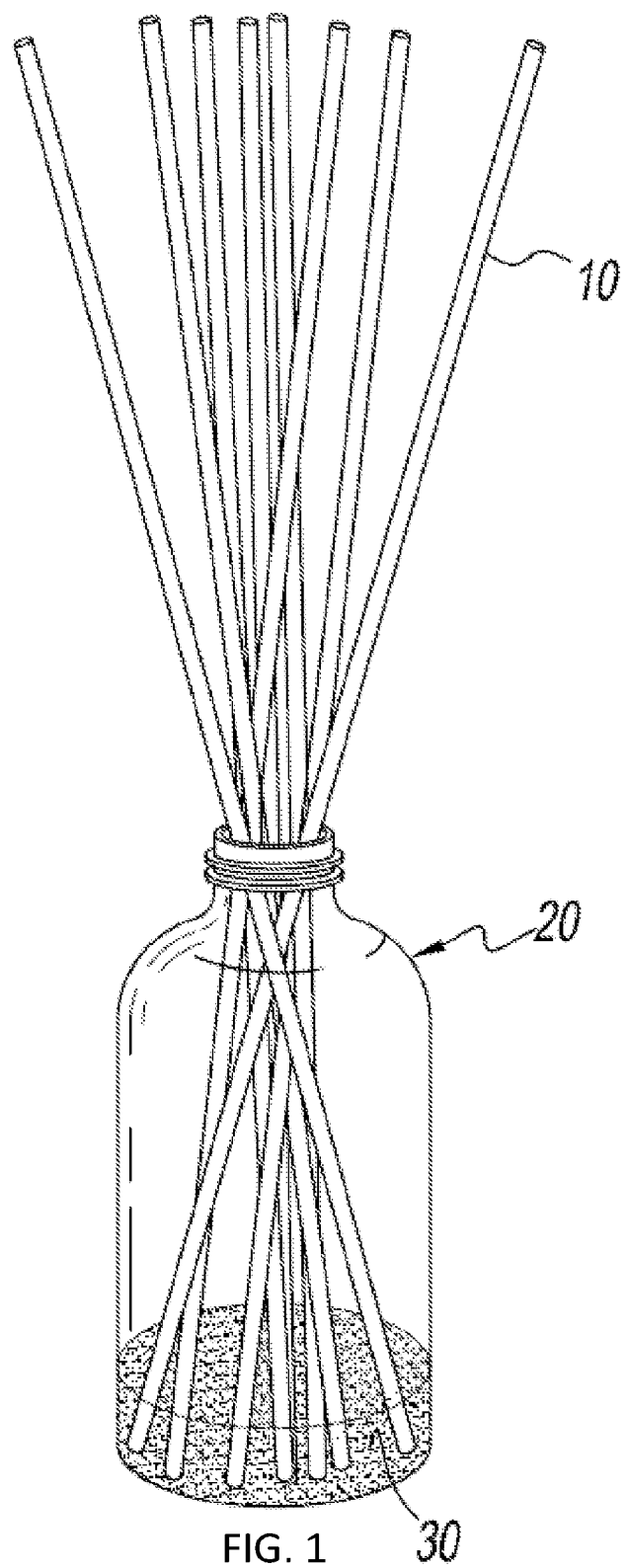
FIG. 1 is a front view of a plurality of wicks in a fragrance container, the fragrance container also holding fragrance solution.

Referring now to FIG. 1, which depicts a plurality of individual artificial or synthetic wicks 10 inserted into a fragrance container 20. The fragrance container 20 holds either a water-based or an organic solvent-based fragrance solution 30. The artificial or synthetic wicks 10 may comprise strands or woven, twisted, braided, or extruded fibers that are natural, synthetic or man-made. The synthetic wick may comprise any length to width ratio, including but not limited to a specific length to width ration of 30.

Figure 3:
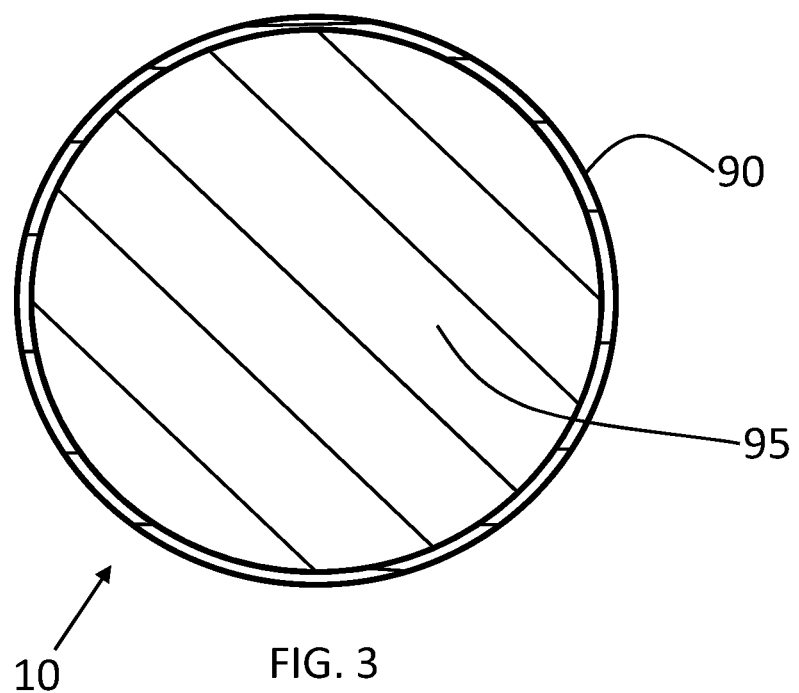
FIG. 3 is a cross sectional view of a wick taken along sectional line 1 in FIG. 2.

The wick 10 may also comprise any combination of synthetic materials at varying densities that allow the wick to both stand upright and absorb or wick 10 the fragrance solution from the fragrance container. In an implementation, the wick 10 may comprise a polypropylene material made through extrusion. The end result of the extrusion process creates a wick 10 wherein an outer shell 90 of the wick 10 is denser, or more stiff/rigid, while an inner, absorbent portion 95 of the wick is less dense, or less stiff/rigid (see FIG. 3). In the same or other implementations, the outer shell 90 may be an annular shell that runs longitudinal along the synthetic wick. The annular outer shell 90 may also, in some implementations, be liquid or gas permeable. The differences in densities between the inner portion 95 and outer portion 90 allow the wick 10 to have the porosity necessary to absorb the fragrance solution 30 in the inner portion 95 at a desirable rate, while remaining upright due to the more dense outer portion 95. By way of example and not limitation, in one implementation the outer portion 90 may comprise a thickness of 0.25 mm and a density of approximately 11.4 g/cubic cm, while the inner portion 95 may comprise a density of approximately 0.31 g/cubic cm. In other implementation, the thickness of the outer portion 90 may vary, while the density remains approximately constant. In yet other implementations, the densities of the outer portion 90 and the inner portion 95 may comprise any density sufficient to provide the wick with the necessary rigidity.

In various implementations, the wick 10 is rigid enough to support its own weight, even after absorbing the fragrance solution 30. Any process or method of manufacture may be utilized to create a synthetic wick 10 with an annular, longitudinal outer shell 90 and an absorbent portion 95 at least partially within the outer shell 90 and extending from a first longitudinal end to a second longitudinal end of the outer shell 90. In other implementations, the outer shell 90 and absorbent portion 95 may comprise any specific densities, so long as the synthetic wick 10 resists deformation due to gravity when one only one end of the synthetic wick 10 is held in place. In other words, if the first longitudinal end may be supported above the second longitudinal end through the structural strength of the synthetic wick, even when the wick is saturated with fragrance solution, without outside support of the wick between the second longitudinal end and the first longitudinal end. In some implementations, the outer shell of the synthetic wick is sufficiently rigid to support the first longitudinal end horizontally extended from the second longitudinal end without outside support between the first longitudinal end and the second longitudinal end.

In another implementation, the wick may comprise a core with sufficient rigidity to support the wick in an upright position, whether or not the wick has absorbed fragrance solution. Such wicks may comprise a variety of materials, including but not limited to a ceramic bisque material, a polypropylene with the same approximate average density throughout the wick, and the like. In particular implementations, the inner rigid core may comprise an outer layer of absorbent wicking material such as the materials offered as possibilities for the absorbent portion 95 discussed herein.

While the cross-sectional thickness of the annular outer shell 90 and the absorbent inner portion may vary in different implementations, in one aspect of the implementation the outer shell 90 comprises a thickness of about 0.30 mm. In other implementations, the thickness may range from 0.25-0.40 mm. In still other implementations the thickness of the outer shell may be less than 0.25 mm or more than 0.40 mm. Having a thin outer shell reduces the weight and increases the ability of the wick to give off fragrance.

In yet other implementations, the synthetic wick 10 may be made through a molding process. In such implementations, the synthetic wick 10 may comprise any length to width ratio, any shape, and an outer shell 90 and an absorbent portion 95 at least partially within the outer shell 90. This and other synthetic wicks 10 may also comprise portions that expand when in contact with the fragrance solution 30. Such expansion may result in various ornamental figures, shapes, or geometric arrangements.

In one implementation, the synthetic wick 10 may comprise a variety of pore-type materials. This and other products may be configured similar to the porous nature of a product such as Styrofoam®-like material. While both the inner portion and outer shell may comprise a Styrofoam®, like material, the densities of two areas may be different (in contrast to typical Styrofoam®, wherein the density is typically uniform throughout). Some implementations may comprise a more porous base to absorb more solution 30. Other implementations may also comprise a portion of the wick 10 on either top or the bottom that expands as solution 30 is absorbed. These areas of expansion may be fashioned into a variety of specific shapes, such as but not limited to spheres, stars, flowers, etc. Average wick 10 density in some, but not all implementations may comprise 0.55 g/cm³. Other implementations may comprise varying average densities. In still other implementations, traditional wood reeds maybe utilized in combination with an LED base 100. As depicted in FIG. 1, the system may comprise wicks 10 or reeds that are placed in the solution 30 and held upright with some assistance of the fragrance container 20. The wick 10 may comprise any diameter or length, although testing has shown that multiple wicks 10 measuring 2.5 mm OD and 12" long perform well in water and solved based fragrance solutions 30.

The wick 10 may further comprise any color, depending on the raw material used to create the wick 10. In most implementations, the wick 10 is substantially white; in some implementations, however, the wick 10 may be dyed any color before, after, or during the extrusion process.

Water based fragrance solutions 30 may comprise any percentage of fragrance oil, though 10% fragrance oil is the typical maximum. Emulsifiers may also be utilized to mix the fragrance oil and the water. Care must be taken with the use of emulsifiers since high levels of emulsifiers may clog the wick 10 after the wick 10 is placed in the fragrance solution 30. The fragrance mixture release rate for water based solution can be over 20 g/day using twelve wicks that measure 2.5 min OD and 12" long. In an implementation, the desired release rate is approximately 0.35 g/day of fragrance oil over a month. Testing has been done on an 8 fl. oz. liquid container volume at a 5% fragrance oil in water based mixture using four wicks. This gives a total fragrance release rate of 0.4 g/day.

Solve based fragrance solution 30 may hold any amount of fragrance oil, although most implementations comprise no more than 25% fragrance oil. Use of a volatile organic compound (VOC) compliant solvent may increase the amount of fragrance oil that may be effectively mixed with the solvent. A typical VOC compliant solvent is Dowanal® DPMA (dipropylene glycol methyl ether acetate), which has a vapor pressure of 0.08 mmHg at 21 degrees Celsius. The DPMA solvent may also be replaced by any number of solvents, including but not limited to Glycol ethers, isopropylmyristate, ethylene glycol, ethyl ether acetate, ketones, and any combination of these or other similar solvents. The fragrance mixture release rate using 20% fragrance oil and 80% Dowanol® DPMA using twelve wicks that measure 2.5 mm OD by 12" long can be 2 g/day. Testing in DMPA solvent based formulas using 30% fragrance oil and 70% DPMA with 12 wicks measuring 12" long yields a total release rate averaging 2.0 g/day. This means that 0.6 g/day of fragrance is released. The solvent based formulas are generally VOC compliant, although in various implementations, other solvents may be utilized. By comparison, reed diffusers using solvent based formulas release about 2.5 g/day initially using 8 reeds. The liquid release rate falls off significantly over time (1.0 g/day) even if the reeds are flipped every week in a 10 fl. oz. bottle. Some never empty the liquid out of the bottle. At 15% fragrance oil concentration, the total fragrance oil release rate is 0.15 g/day. By comparison, most electric plug diffusers release about 0.3 g/day of fragrance oil.

In various implementations, the fragrance solution 30 may comprise any variety of solutions that contain fragrance from any source. In an implementation, the fragrance solution comprises a non-aqueous active volatile liquid solution. Organic solvents such as ester, glycol, and the like may be combined with fragrance oil in some implementations. In other implementations, fragrance oil may combine with other solvents or carriers such as ethanol, polyethylene glycol, propylene glycol, vegetable oil, mineral oil, or other oils. Essential oils may also be used in the fragrance solutions 30 of various implementations to impart any particular scent or aroma. The essential oil may comprise any concentrated, hydrophobic liquid comprising aroma compounds from plants or other sources. Volatile oils, ethereal oils, or aetherolea oils may also be utilized in various fragrance solutions 30. The concentrations of the fragrance oil and the solvent or carrier in the final solution may vary. In an aspect of the implementation, the final solution comprises approximately 10%-20% fragrance oil and approximately 75%-85% solvent or carrier. In one specific embodiment, and not by limiting example, the final solution may comprise 78.5% organic solvent, 16.5% fragrance oil, 3.5% isopropyl alcohol and 1.5% water.

The fragrance solution 30 may also comprise a colorant that would change the color of a wick 10 after the wick 10 is placed in the fragrance solution 30. By way of example and not limitation, a dyed fragrance mixture 30 may turn a white wick 10 the same color as the dye in the fragrance solution 30. In such implementations, the dye may change the color of the wick 10 as the wick 10 absorbs fragrance solution 30 and the dye bonds to the material of the wick 10.

The fragrance container 20 may comprise any container suitable for holding the fragrance solution 30 while resting on the base. In various implementations, the container 20 may be comprised of a translucent or transparent material, while in other implementations, the container 20 may be opaque. The fragrance container 20 may be comprised of any material, such as glass, crystal, ceramic, metal, earthware, porcelain, terracotta, or even polymers like polyproplylene, polyethylene, nylon, and the like. Various implementations may use fragrance containers 20 configured to maximize or minimize heat transfer from the base to the fragrance solution. For example, containers with a thinner base or base made with different materials may facilitate heat transfer. The fragrance container may further comprise any shape that allows wicks or reeds to be placed within the container. In an embodiment, the container comprises a wide bottom and a narrow neck, thus allowing the wick or reed to stand more upright.

Figure 2:
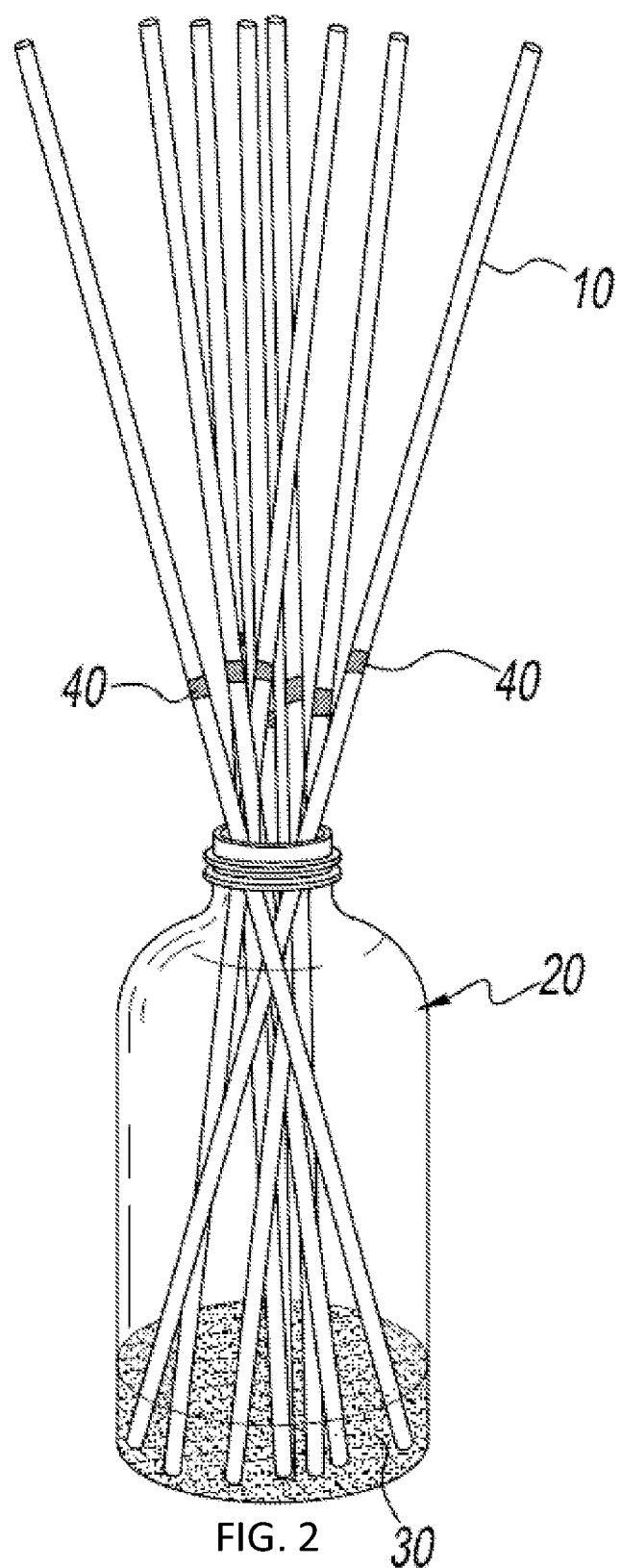
FIG. 2 is a front view of a plurality of wicks color bands in a fragrance container, the fragrance container also holding fragrance solution.

Referring now to FIG. 2, which depicts a plurality of wicks 10 with color bands 40, the wicks 10 being placed in a fragrance container 20 holding fragrance solution 30. As used herein, the terms "band" and "bands" are not intended to imply any particular shape or orientation for the colorant on the wicks but are intended to encompass colorant applied to a wick through any pattern, thickness or order including, but not limited to, continuous bands that circumscribe the wick, disjointed bands that circumscribe the wick but are not continuous, one or more polka-dots, triangles, squares, circles, stars and/or other shaped colorant portions applied on one or more portions of the wick at any location and on any or some or all sides of the wick. The term "band" is used only to imply that the colorant-marked portions of the wick will generally begin at some linear distance from an end of the wick, that distance being the distance to the beginning of the first color band. In various implementations, the wick 10 may further comprise one or more color bands 40 comprised of any type of colorant, such but not limited to any ink, pigment, or dye.

In some implementations, the color band may be approximately 1/8" thick, while in other implementations, the color band may comprise any thickness or length. In one aspect, a color band 40 that is 1/4" is typically sufficient to change the wick color above the location of the color band 40 during use. The colorant may comprise any of a variety of colors.

When a wick 10 with a color band 40 is inserted into a fragrance solution 30, the fragrance solution 30 is drawn up into the wick 10 through capillary or other forces. Although the particular implementations of wicks 10 shown in FIGS. 1-3 have a circular cross-section, this is not a requirement of the wick. Particularly because some implementations of wicks described herein are made of synthetic materials, and many implementations are formed through an extrusion process, the wicks may be formed to any cross-sectional shape such as, by non-limiting example, square, rectangular, oval, star, and hexagonal or any other polygonal shape. In various implementations, the colorant is spread throughout the wick 10 when the fragrance solution reacts with the ink. The spread of the ink throughout the wick 10 may be facilitated by the alcohol present in the solution 30, which acts to mix with and spread the ink. In other implementations, the colorant may be invisible until the colorant reacts with the fragrance solution 30. In such implementations, the colorant in the color band 40 and the fragrance solution may comprise any variety of chemicals, such as but not limited to complementary phenol-formaldehyde compounds that cause the color band 40 to change colors when the fragrance solution reaches it or even, in particular implementations, cause the color band 40 to change from a clear color to a more visible color band when the fragrance solution reaches it. In still other implementations, the colorant may change color when it reacts with the fragrance solution. The color may be comprised of any type of colorant, such as but not limited to non-toxic permanent dye, pigment, or ink In an implementation, the colorant may comprise an ink comprising at least one of n-propanol, n-butanol, and diacetone used in combination with different dyes. These inks work by evaporation of the carriers in the colorant after the ink is applied to the wick or reed. When the fragrance formula travels through the dyed color band on either the reed or wick, the components such as esters, alcohols, ketones, and other organics move the dye through the wick. In other implementations, the ink may comprise xylene, toluene, alcohol, cresol, ethanol, or other solvents.

In implementations utilizing a water based fragrance solution 30, the color band 40 must comprise a water soluble colorant. Water soluble colorants may comprise any water based dyes, inks, pigments, and the like, including but not limited to acid colorants, basic colorants, direct colorants, disperse dyes, and natural dyes.

Figure 4:
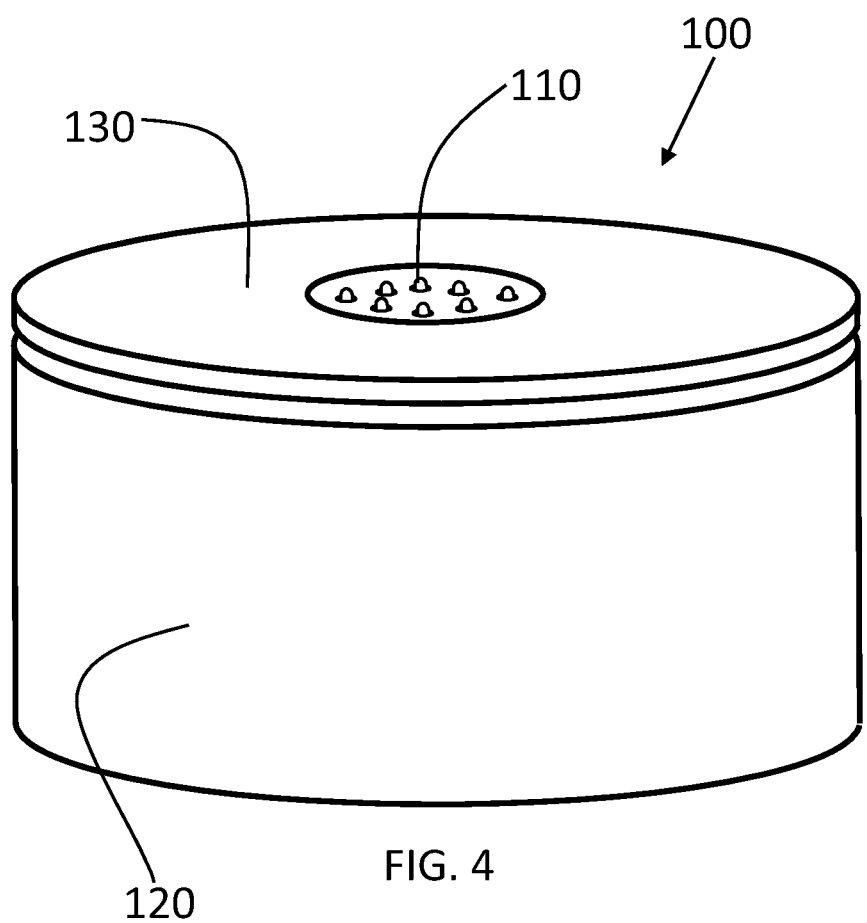
FIG. 4 is a front view of an illuminated base.

In an aspect, various implementations may further comprise a base 100. An implementation of the base 100 is shown in FIG. 4. In the implementation shown, the base comprises a flat, rotating surface 130 upon which the fragrance container 20 may rest. Variations of these and other features are described herein. The base 100 may comprise any system that allows the fragrance container 20 to rest flat on a surface 130. In various implementations, the base 100 may comprise an electric or battery powered motor that rotates a surface 130 of the base 100. In various implementations the motor may be enclosed in the base housing 120. The base surface 130 that rotates may in various embodiments be the same surface 130 on which the fragrance container 20 rests. A person having skill in the art will recognize how the motor rotates the surface 130 of the base 100. A rotating surface 130 provides sufficient air flow past the wicks 10 or reed diffusers such that a fan is not necessary to efficiently disperse the fragrance. The speed at which the surface 130 rotates may vary in different implementations. Some bases 100 may be configured such that the surface 130 rotates at one set speed, for example but not by way of limitation, a 360 degree rotation every minute. Various implementations may comprise any speed of rotation. Other implementations may have a switch that allows a user to choose a specific rotational speed setting, such as but not limited to slow, medium, fast. Increasing the speed of rotation may facilitate the dispersal of fragrance around a room, thus allowing a user to control the level of fragrance dispersed in a room. The rotating surface 130 may further comprise any material and any shape, such as but not limited to a circle, square, oval, etc.

In various implementations the base 100 may further comprise light-emitting-diodes (LED) 110. LEDs 110 may or may not be used in combination with the rotating surface 130. In an implementation, a surface 130 of base may be comprised of a glass or other clear material with at least one LED 110 below the glass, such that the fragrance container may rest on the surface 130 of the base 100 above the LED 110. The entire glass surface may be clear in some implementations; in other implementations, only the portion of the surface 130 above the LED 110 is clear, while the rest of the surface 130 may have a mirror-like reflective quality. The surface 130 may comprise any material suitable to resist deformation due to the heat caused by the LED 110, such as but not limited to glass, crystal, or any other transparent or translucent material. Although LEDs are disclosed for particular implementations of the disclosure, alternatively small halogen, incandescent or compact florescent ("CFL") bulbs may be used. These types of bulbs may create a greater heat factor for the unit, but also use more power and generally do not last as long as LEDs.

The base 100 may comprise any number of LEDs 110 in any configuration or pattern. In an implementation, the base 100 comprises seven LEDs 110 clustered near the center of the surface 130 the fragrance container 20 is to rest on. In other implementations, LEDs 110 may be spread across the entire surface 130. The LEDs 110 may comprise any color and may change color while the motor of base 120 is turned on. The LEDs 110 may generate power from a battery, an electric plug, or any other suitable power source known to one of skill in the art.

In some implementations, all the LEDs 110 present on the base 100 are either on or off. In other implementations, the user may control how many LEDs 110 are on or off. Control over the number of LEDs 110 on or off allows the user to have some control over the amount of heat being put into the system of fragrance dispersal. LEDs 110 may provide heat to the fragrance container 20, which in turn improves fragrance dispersal. By way of example but not limitation, in a base 100 with seven LEDs 110, the temperature of the fragrance solution 30 averages 78.3 degrees Fahrenheit, while the temperature of the fragrance solution 30 without any LEDs 110 average 72.7 degrees Fahrenheit (dependant on ambient room temperature). In some embodiments, heating resistors may also be implemented in the base to further facilitate the transfer of heat from the base 100 to the fragrance solution 30, and thus increase the amount of fragrance dispersed into the air. The motor within the base 100 may also provide heat to the system while the motor is rotating the surface 130.

Using the combination of the rotating surface 130 and LEDs 110 may result in the solution 30 dispersing faster; by way of example and not limitation, in a system utilizing a seven LEDs 110 and a rotating surface, the loss of solution 30 was at least 30% more than without such a system. For example, in one study, a 4.5 gram fragrance solution 30 loss was observed when using synthetic wicks 10 in combination with an LED base 100. In contrast, only a 3.3 gram fragrance solution 30 loss was observed when using the same number of synthetic wicks 10 in the same ambient environment, but without the LED base 100. In a study utilizing wood reeds, a 3.5 gram fragrance solution loss was observed when used in combination with an LED base 100; a 2.4 gram fragrance solution 30 loss was observed when used in without an LED base 100 in the same ambient environment.

As the mass of the fragrance solution 30 remaining in the container 20 decreases, the temperature of the remaining solution 30 increases. This can be explained by the formula of $Q=mc\Delta T$, wherein Q equals the heat added to the system, c equals the specific heat of the fragrance, m equals the mass of the solution, and $\Delta T$ equals the change in temperatures. Q remains constant as the same heat is constantly applied to the system, while c remains constant as the specific heat of fragrance solution 30. Therefore, as the mass of the fragrance solution 30 drops, the change in temperature increases. An increased temperature further increases the efficiency of the system by facilitating the absorption and release of more fragrance.

Figure 5:
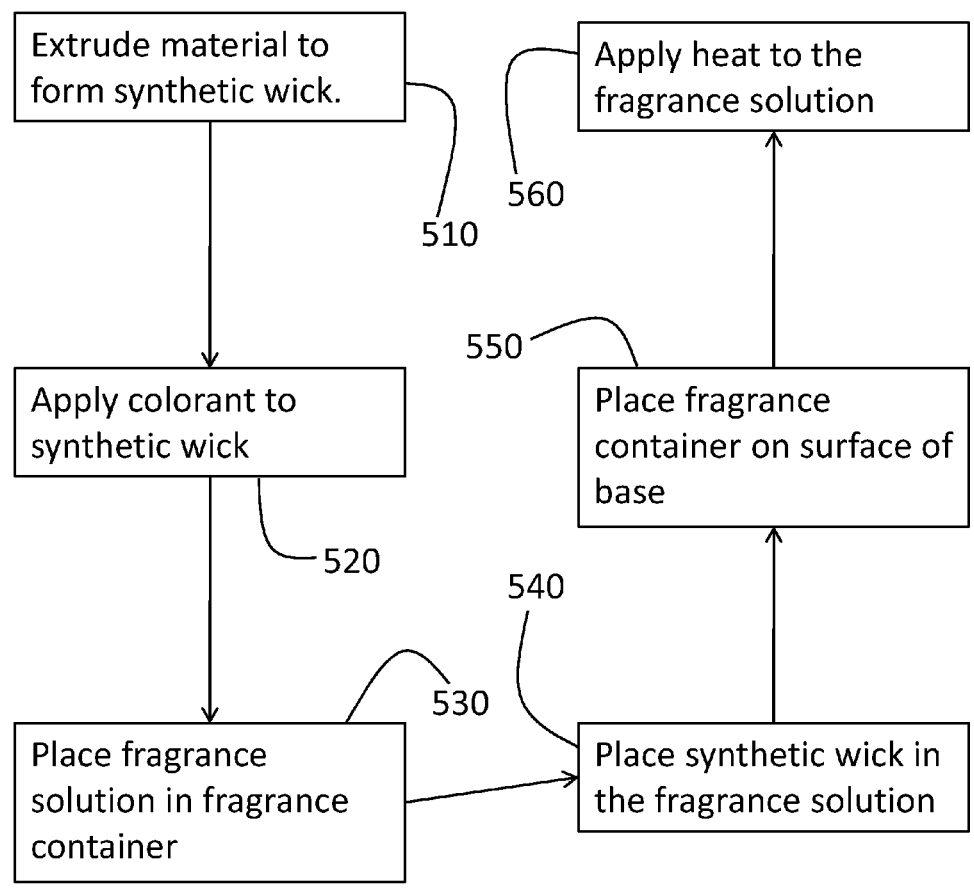
FIG. 5 is a flowchart depicting a method of diffusing fragrance.

Referring now to FIG. 5, a flow chart diagram of a method of dispensing a fragrance vapor. In an implementation, the method may comprise the act of placing a fragrance solution in a fragrance container (step 530). The fragrance solution, in various implementations, may comprise a solvent and a fragrance oil. The solvent may be either a water-based solvent or an organic-solvent, and the fragrance oil may comprise any scented oil, such as but not limited to essential oils.

The method may further comprise the act of placing at least one synthetic wick in the fragrance solution (step 540). According to an aspect of the implementation, the at least one synthetic wick may comprise a length to width ratio of at least 30 and being formed of synthetic fibers, an annular longitudinal outer shell, and an absorbent portion at least partially within the outer shell. In other implementations, the wick may comprise any length to width ratio. The absorbent portion may also extend from a first longitudinal end to a second longitudinal end of the outer shell. In an implementation, the outer shell is more dense than the absorbent portion and sufficient to vertically support the first longitudinal end above the second longitudinal end without additional support above the second longitudinal end.

The method may further comprise the act of applying a colorant to the at least a portion of the outer shell of the at least one synthetic wick (step 520). The area of the wick where the colorant is applied may be referred to as a color band, although in some implementations, the color band does not go entirely around the wick. Once in a fragrance solution, the synthetic wick may absorb the fragrance solution and, depending on the properties of the colorant and fragrance solution, the colorant may change the color of at least a portion of the synthetic wick.

The method may further comprise the act of placing the fragrance container on a substantially planar surface of a base (step 550). In an implementation, the base may comprise at least one LED visible through the substantially planar surface. The base may further comprise a motor configured to rotate the planar surface. In various implementations, the method may further comprise applying heat to the fragrance solution (step 560) to increase dispersal of the fragrance vapor. Heating the fragrance solution may be accomplished in various ways, including but not limited to LED generated heat from the base, heating elements in the base, heating elements in the fragrance container, and the like.

In an implementation, the method may further comprise the act of extruding material, such as polypropylene, to create the synthetic wick (step 510). In other implementations, the method may further comprise the act of molding polypropylene to create the synthetic wick. In still other implementations, any suitable material may be substituted for polypropylene and be used in the extruding or molding process. In implementations utilizing extrusion, molding, or other techniques, the process may create an outer shell that is more dense, stiff, or rigid than the more absorbent inner portion. In some instances, this is due to the heating of the synthetic fibers for a specific amount of time, which results in a less porous but more rigid out shell surround the more porous inner portion. Rather than a synthetic wick, a reed wick may alternatively be used or any other wick having any other properties as those disclosed or described throughout this disclosure.

It will be understood that implementations are not limited to the specific components disclosed herein, as virtually any components consistent with the intended operation of a method and/or system implementation for dispersing a fragrance may be utilized. Accordingly, for example, although particular wicks, reeds, fragrance solutions, and colorants may be disclosed, such components may comprise any shape, size, style, type, model, version, class, grade, measurement, concentration, material, weight, quantity, and/or the like consistent with the intended operation of a method and/or system implementation for a fragrance diffuser may be used.

In places where the description above refers to particular implementations of wicks, colorants, or solutions, it should be readily apparent that a number of modifications may be made without departing from the spirit thereof and that these implementations may be applied to other wicks, colorants, or solutions. The accompanying claims are intended to cover such modifications as would fall within the true spirit and scope of the disclosure set forth in this document. The presently disclosed implementations are, therefore, to be considered in all respects as illustrative and not restrictive, the scope of the disclosure being indicated by the appended claims rather than the foregoing description. All changes that come within the meaning of and range of equivalency of the claims are intended to be embraced therein.

The invention claimed is:

1. A fragrance vapor dispenser, comprising:
   at least one synthetic wick comprising a length to width ratio of at least 30 and being formed of synthetic fibers, the at least one synthetic wick further comprising a longitudinal outer shell and an absorbent portion at least partially within the outer shell and extending from a first longitudinal end to a second longitudinal end of the outer shell, and at least one color band, wherein the outer shell is more dense than the absorbent portion and sufficiently rigid to vertically support the first longitudinal end above the second longitudinal end without additional support above the second longitudinal end;
   wherein the at least one color band comprises a colorant absorbed through the outer shell at least partially into the absorbent portion, the color band having a longitudinal width of at least ⅛ inch.

2. The fragrance vapor dispenser of claim 1, wherein at least a portion of the synthetic wick is within a fragrance container containing a fragrance solution, the fragrance solution comprising a solvent and a fragrance oil.

3. The fragrance vapor dispenser of claim 2, wherein the solvent comprises a water-based solvent.

4. The fragrance vapor dispenser of claim 2, wherein the solvent comprises an organic solvent.

5. The fragrance vapor dispenser of claim 2, further comprising a base comprising a substantially planar surface upon which the fragrance container sits and a motor that rotates the substantially planar surface.

6. The fragrance vapor dispenser of claim 5, the base further comprising at least one light emitting diode (LED) visible through the substantially planar surface, wherein a temperature of the fragrance solution increases when the at least one LED is on.

7. The fragrance vapor dispenser of claim 1, wherein the outer shell and the absorbent portion are the same synthetic material.

8. The fragrance vapor dispenser of claim 7, wherein the synthetic wick comprises extruded polypropylene.

9. The fragrance vapor dispenser of claim 8, wherein the synthetic wick further comprises a porous material.

10. The fragrance vapor dispenser of claim 1, wherein the diameter of the at least one synthetic wick is between 1/16 inch and 1/4 inch.

11. The fragrance vapor dispenser of claim 3, wherein the fragrance solution further comprises a fragrance solution colorant, wherein the synthetic wick changes color as the fragrance solution is absorbed by the at least one synthetic wick and the fragrance solution dye spreads throughout the wick.

12. The fragrance vapor dispenser of claim 1, further comprising at least one second color band on the at least one synthetic wick.

13. The fragrance vapor dispenser of claim 12, wherein the at least one second color band is spaced more than 1/16" from the first color band.

14. The fragrance vapor dispenser of claim 1, wherein the at least one synthetic wick is shaped by a molding process.

15. A method of dispensing a fragrance vapor, comprising:
applying a colorant to at least a portion of a longitudinal outer shell of at least one synthetic wick, the at least one synthetic wick comprising a length to width ratio of at least 30 and being formed of synthetic fibers and comprising an absorbent portion at least partially within the outer shell and extending from a first longitudinal end to a second longitudinal end of the outer shell, wherein the outer shell is more dense than the absorbent portion and sufficiently rigid to vertically support the first longitudinal end above the second longitudinal end without additional support above the second longitudinal end;
placing a fragrance solution in a fragrance container, the fragrance solution comprising a solvent and a fragrance oil;
placing at least one synthetic wick in the fragrance solution; and
changing a color of at least a portion of the synthetic wick at a portion of the synthetic wick to which the colorant was not applied as the wick absorbs the fragrance solution adjacent to the portion of the synthetic wick to which the colorant was applied.

16. The method of claim 15, further comprising:
placing the fragrance container on a substantially planar surface of a base, the base comprising at least one light emitting diode (LED) visible through the substantially planar surface and a motor configured to rotate the planar surface.

17. The method of claim 16, further comprising:
applying heat to the fragrance solution by turning on the at least one LED increase a rate of fragrance dispersal.

18. The method of claim 17, further comprising extruding polypropylene to create the synthetic wick.

19. A fragrance vapor dispenser, comprising:
at least one molded wick comprising synthetic fibers, an outer shell, an absorbent portion at least partially within the outer shell and extending from a first end to a second end of the at least one wick, and a color band;
wherein the outer shell is more dense than the absorbent portion and sufficiently rigid to vertically support the first end above the second end without additional support for the wick above the second end; and
wherein the color band comprises colorant absorbed through the outer shell at least partially into the absorbent portion, the color band having a width of at least 1/8 inch.

20. The fragrance vapor dispenser of claim 19, wherein at least a portion of the molded wick is within a fragrance container containing a fragrance solution, the fragrance solution comprising a solvent and a fragrance oil.

21. The fragrance vapor dispenser of claim 20, further comprising a base comprising a substantially planar surface upon which the fragrance container sits, a motor that rotates the substantially planar surface, and at least one light emitting diode (LED) visible through the substantially planar surface.

22. A fragrance vapor dispenser, comprising:
at least one wooden reed, wherein at least a portion of the wooden reed is within a fragrance container containing a fragrance solution, the fragrance solution comprising a solvent and a fragrance oil; and
a base comprising a substantially planar surface upon which the fragrance container sits, a motor that rotates the substantially planar surface, and at least one light emitting diode (LED) visible through the substantially planar surface, wherein a temperature of the fragrance solution increases when the at least one LED is on.

* * * * *